US007513868B1

(12) United States Patent
Fontenot

(10) Patent No.: US 7,513,868 B1
(45) Date of Patent: Apr. 7, 2009

(54) STIMULATION AID

(76) Inventor: Tony Fontenot, 1518 Jamie St., Mamou, LA (US) 70554

( * ) Notice: Subject to any disclaimer, the term of this patent is extended or adjusted under 35 U.S.C. 154(b) by 0 days.

(21) Appl. No.: 11/799,716

(22) Filed: May 3, 2007

Related U.S. Application Data

(60) Provisional application No. 60/801,916, filed on May 19, 2006.

(51) Int. Cl.
*A61F 5/00* (2006.01)

(52) U.S. Cl. ........................................................ 600/38

(58) Field of Classification Search ............. 600/38–41; 128/897, 898
See application file for complete search history.

(56) References Cited

U.S. PATENT DOCUMENTS

| | | | |
|---|---|---|---|
| 5,690,603 A | 11/1997 | Kain | |
| 6,132,366 A | 10/2000 | Ritchie et al. | |
| 6,991,599 B2 * | 1/2006 | Hudson | 600/38 |
| 2003/0097041 A1 | 5/2003 | Ritchie et al. | |

* cited by examiner

*Primary Examiner*—Samuel G Gilbert
(74) *Attorney, Agent, or Firm*—Robert N. Montgomery

(57) ABSTRACT

A sex aid apparatus is disclosed utilizing an extended geometrical shaped handle for interchangeable attachment to intra-vaginal or anal penetration appliances and the manual manipulation thereof.

13 Claims, 5 Drawing Sheets

STIMULATION AID

1. FIELD OF THF INVENTION

This is a Non-provisional application relating to provisional application No. 60/801,916 filed May 19, 2006. This invention relates generally to a sex aid and more particularly to a manually manipulated intra-vaginal apparatus with quick-change appliances.

2. GENERAL BACKGROUND

Various types of sexual aids for use in sexual stimulation have been in use since the dawn of man. A great number of mechanical and manual manipulative devices have been patented having a variety of shapes for both vaginal and anal penetration. Many such devices, also called dildos, are designed to simulate the male sexual organ in a manner so as to increase sexual stimulation through known methods and practices. Although the use of such devices is very well known within the art and are used by both men and women alone or as couples, women often seek solitary sexual gratification by artificial means for a number of reasons. For example, sexual dysfunction between married partners may render conventional sex between partners impossible due to disease and resulting medications. Further, a great many women simply have no partners and do not wish to subject themselves to potential harm from strangers who may be disease carriers.

Conventional therapeutic devices currently available include various types of vibrators and automated mechanical sex aids. Many of these sex aids require the use of another partner, either male or female. Such aids also include electro-mechanical reciprocating devices that are mounted stationary using springs or elastic harnesses and the like. Such devices generally require unnatural positioning and are awkward to use at best. Many are simply artificial, hand held tools, such as plastic or rubber vibrators, that provide stimulation but fail to gratify a woman who wants not only the ultimate gratification but also the feeling that she is actually having sex with a partner. Although there are a large number of sexual devices that closely resemble the male sex organ, they have been found to be heavy, expensive, and require a great deal of awkward manipulation and imagination to achieve any significant gratification. The problem with manually manipulated devices is that they require the user to hold a portion of the appliance in a manner that prevents the user from relaxing during penetration. In addition most appliances are not interchangeable to allow for a variety of shapes to be quickly exchanged and used with the same apparatus. Therefore, a long-felt but unfilled need still exists in the art for a therapeutic apparatus that more closely resembles sexual intercourse and that can be used at any tempo, manner, or degree of gentleness or roughness, as desired, by the user in a more natural position.

The present invention solves many of the unnatural positioning problems associated with manual manipulation of the prior art sex aids.

3. SUMMARY OF THF INVENTION

The improved sex aid disclosed herein may utilize many of the known manual sexual stimulation devices shapes currently known within the art as attachments to the manipulator handle described. The device utilizes a shaped handle having a flexible intermediate member that is attachable to a variety of intra-vaginal appliances. Application of the device and its general purpose, as described subsequently in greater detail, provides the user with more control and in a more relaxed position than heretofore known.

4. BRIEF DESCRIPTION OF THE DRAWINGS

For a further understanding of the nature and objects of the present invention, reference should be made to the following detailed description taken in conjunction with the accompanying drawings, in which, like parts are given like reference numerals, and wherein.

Figure 1:
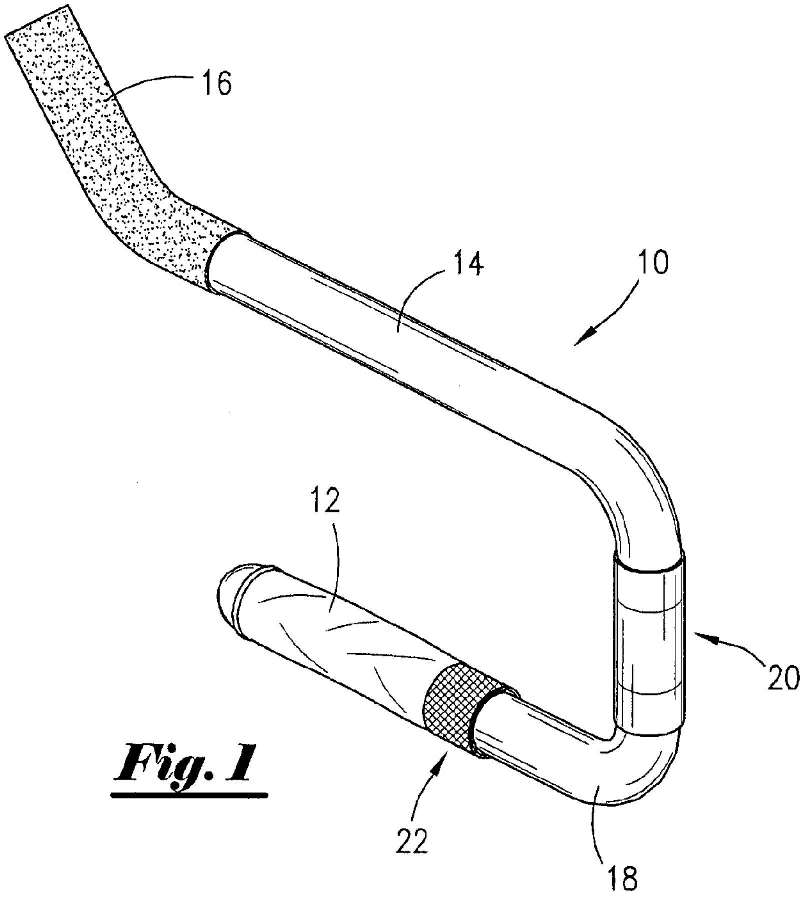
FIG. 1 is an isometric view of the preferred embodiment.
Figure 11:
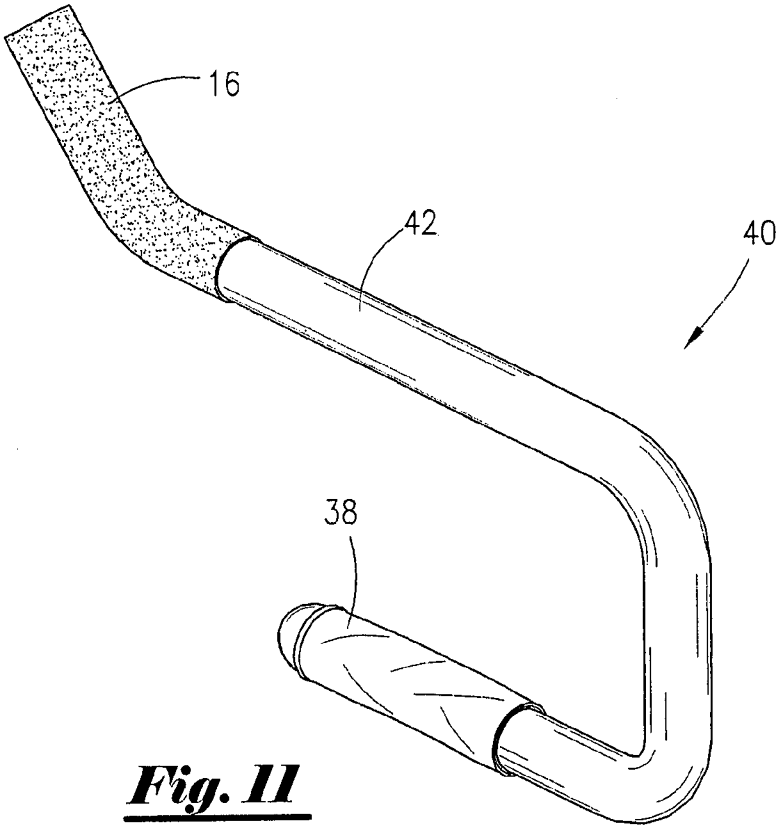

FIG. 11 an isometric view of another embodiment of FIG. 1; and

Figure 12:
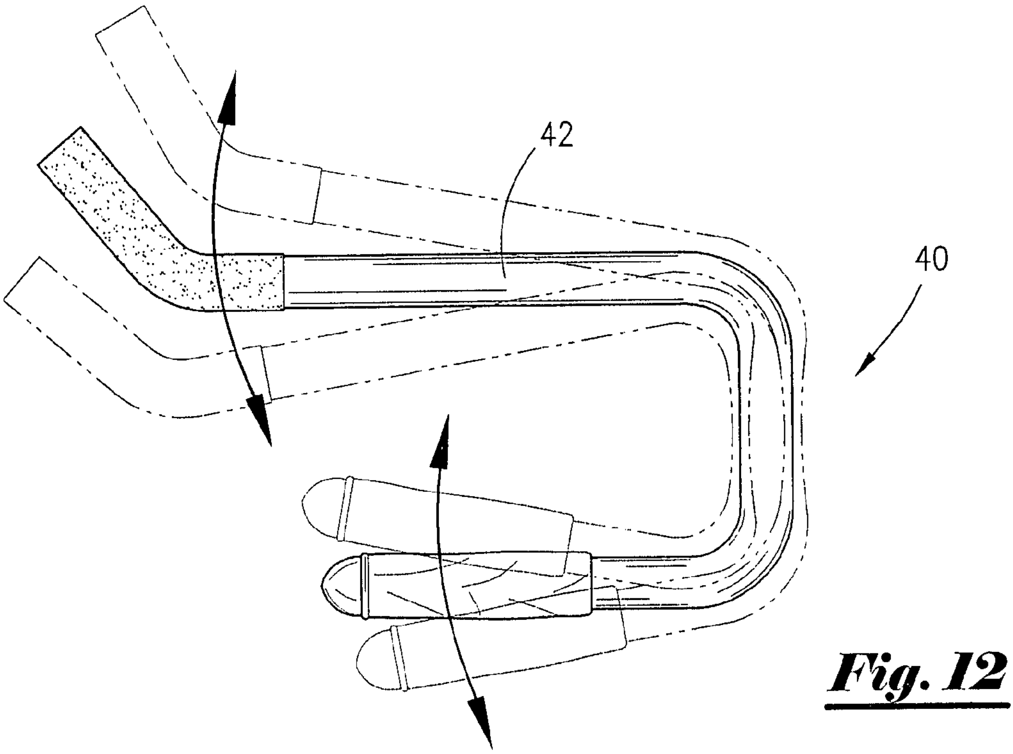

FIG. 12 is a vertical side view of the embodiment shown in FIG. 11.

5. DETAILED DESCRIPTION OF THF PREFERRED EMBODIMENT

Figure 2:
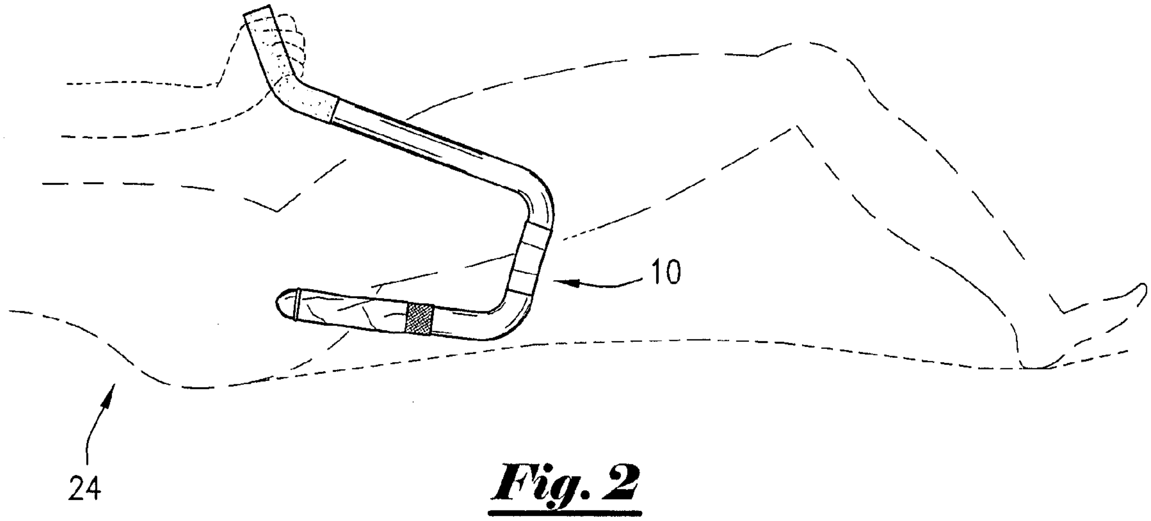
FIG. 2 is a side elevation view of the preferred embodiment in position by a user.
Figure 9:
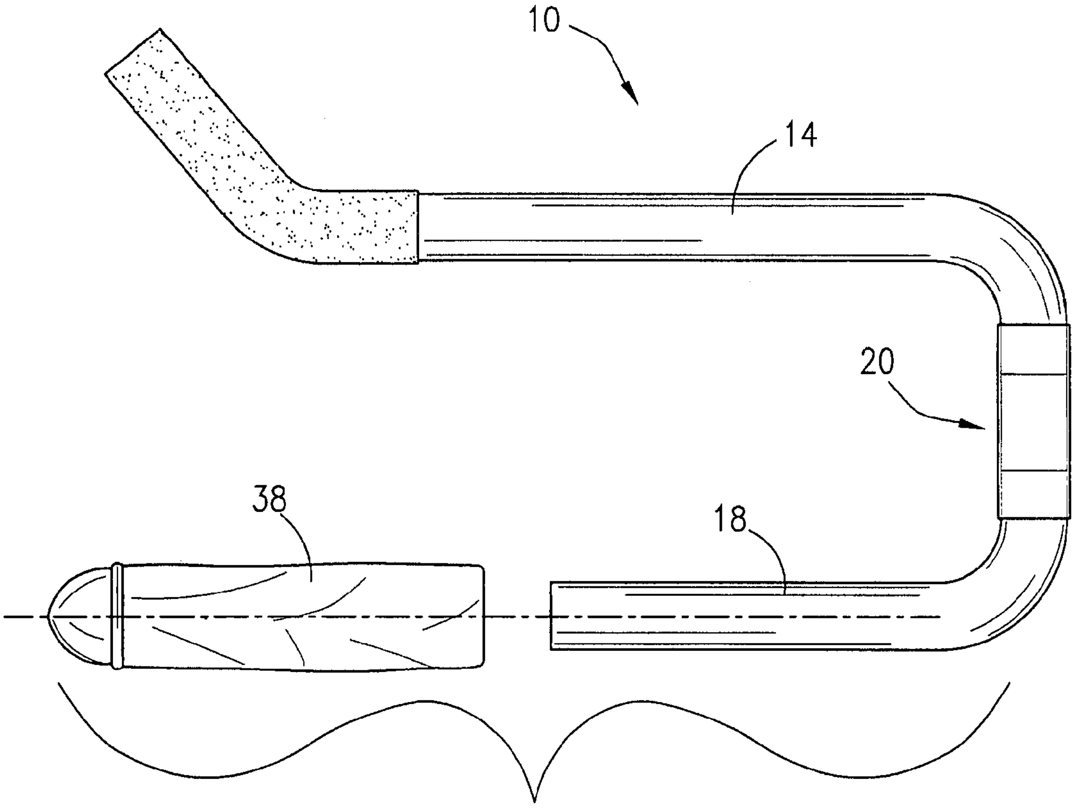
FIG. 9 is a side elevation view of an alternative embodiment without quick snap connection and tubular sleeve member.

The Sexual aid assembly 10 as shown in FIG. 1 is an extended handle assembly for attaching a variety of detachable sexual aid appliances 12. The handle assembly 10 includes a first one-half inch to three-quarter inch diameter tubular member 14 with one end having a 90 degree bend the opposite end having a 30 to 45 degree outward offset or kick located at an obtuse angle preferably of about 45 degrees at the end opposite the 90 degree bend. The second one-half inch to three-quarter inch diameter tubular member 18 also has a 90 degree bend at one end and open at the other as shown in FIG. 9 or may be fitted with a portion 32 of the quick coupling 22 seen in FIG. 6. The two tubular members 14, 18, are connected at their 90-degree bend portions by a flexible connector assembly 20. This configuration forms a “J” shaped handle attachment for a variety of phallus shaped sexual appliances 12 thus placing the user 24 in a more relaxed position as illustrated in FIG. 2, and manipulated with only one hand.

Figure 3:
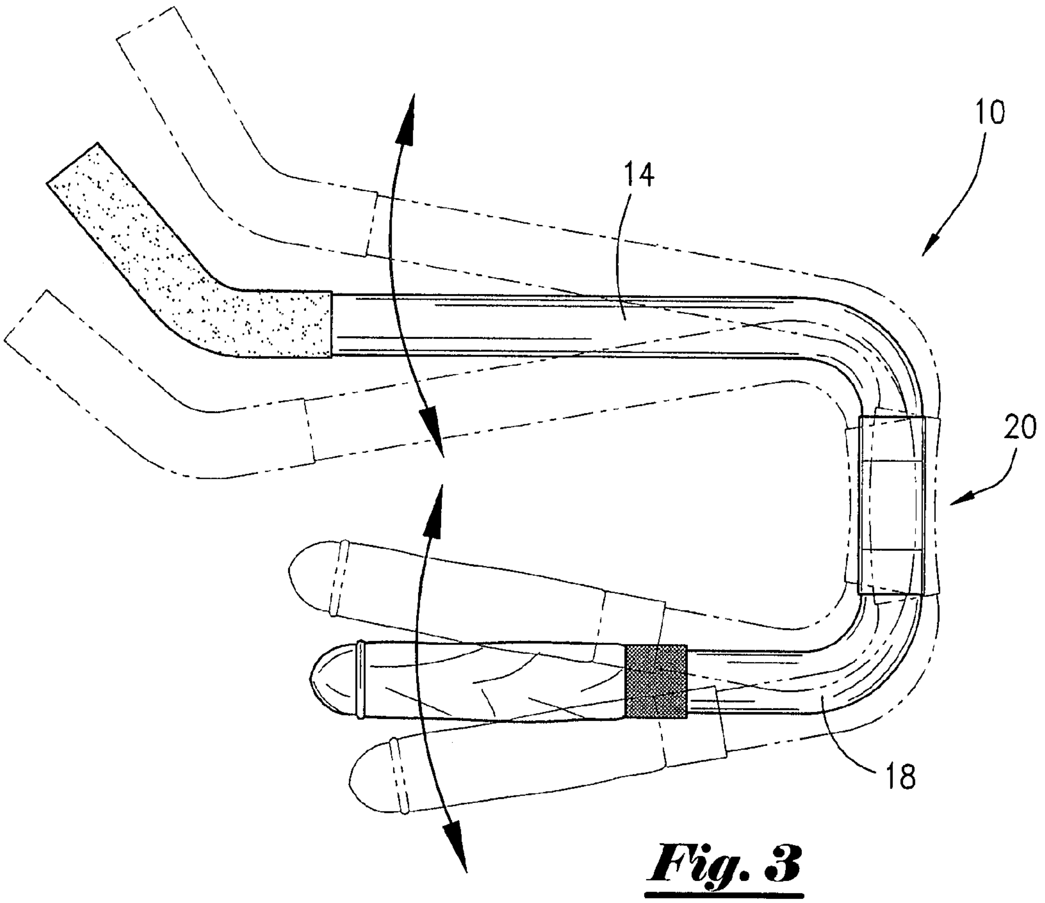
FIG. 3 is a side elevation view of the preferred embodiment showing flexibility.

The tubular members may be a polymer or a polymer coated metal tube. It is also anticipated that the first upper and second lower tubular members 14, 18 and flexible joint 20 could be replaced with a single piece of cylindrical polymer rod, as seen in FIG. 11. In either case a covering or handle 16 is provided for the offset kicked out end of the first or upper tubular member 14. The covering 16 may be a removable foam sleeve or a relatively soft polymeric material. As can be seen in FIG. 3 the first upper tubular member 14 and the lower or second tubular member 18 may be independently flexed relative to each other due to the flexible joint 20.

Figure 4:
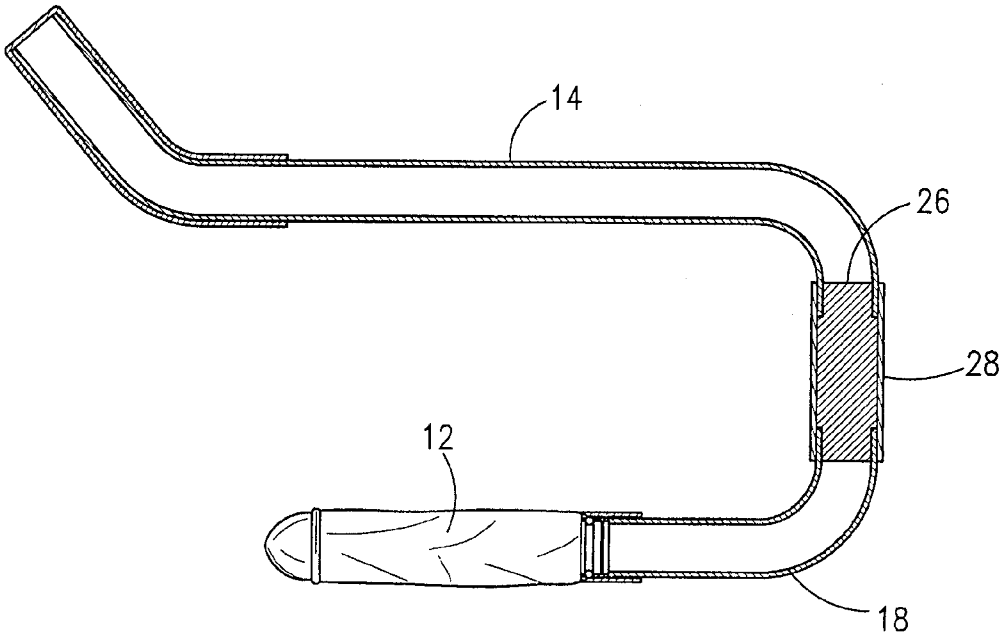
FIG. 4 is a partial side elevation, cross section view of the preferred embodiment.

Looking at FIG. 4 we see that the flexible joint 20 is a relatively pliable polymeric member 26 sized, inserted and fixed within the tubular members 14, 18. The polymeric member 26 should have sufficient length to allow for flexure of the tubular members 14, 18 in all planes as illustrated in FIG. 3.

An external sleeve 28 may be used to cover the polymeric flexure member 26. Since sanitization is an important factor in the design, care should be taken to insure that all members could be easily washed and disinfected.

Figure 5:
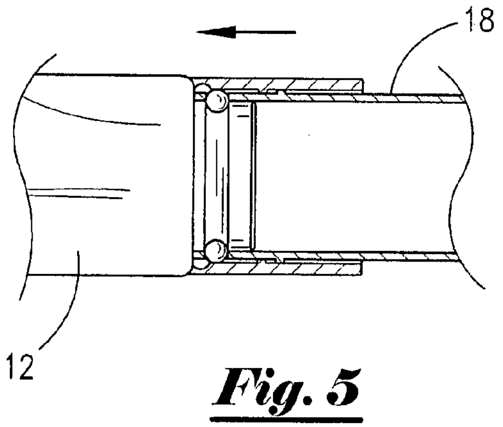
FIG. 5 is a partial cross section view of the quick snap connection with appliance attached.
Figure 6:
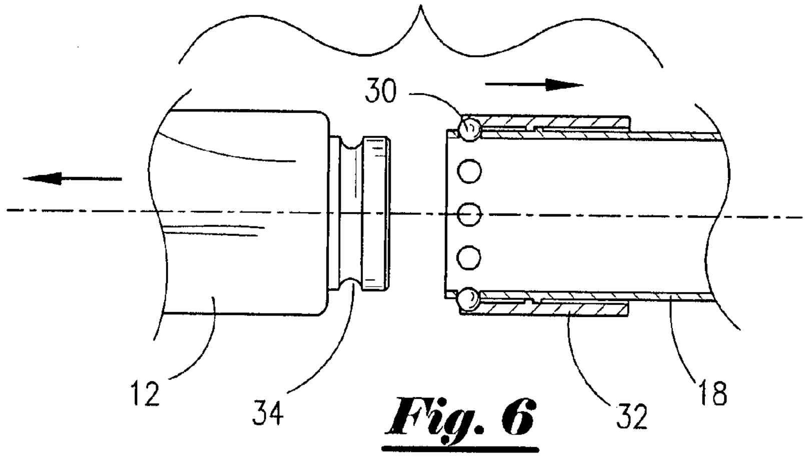
FIG. 6 is a partial cross section view of the quick lock connection with appliance detached.

Although a variety of quick interlocking devices may be used to connected the appliances 12 to the lower tubular member 18, a slip lock type of quick connect 22, as seen in FIG. 1 and shown in FIGS. 5 and 6, is an example of a quick change connection for the appliances 12. As shown in FIG. 6, such connectors utilize a first connector portion 32 attached to the tubular member 18 having a series of balls 30 located in individual holes and captured therein by a spring biased sliding sleeve 32. A second connector portion 34 is attached to the appliance member 12 having a channel therein for receiving the balls 30. Therefore when the first and second connector portions 32, 34 are connected the balls 30 are retained within the channel by the sliding sleeve 32. Twist lock connectors and other types of snap-on connectors may be used as well.

Figure 7:
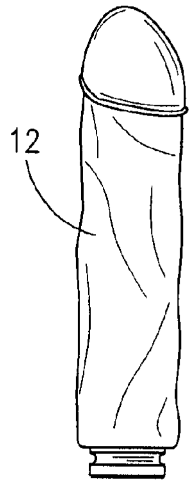
FIG. 7 is slide view of a typical appliance.
Figure 8:
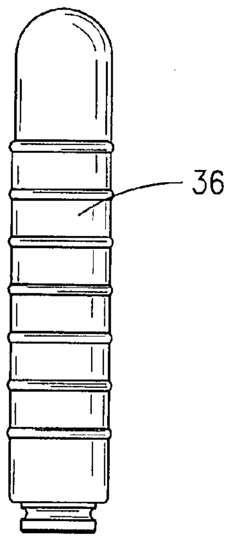
FIG. 8 is slide view of an alternative appliance.

Obviously any type of body cavity insertion member can be used as an appliance 12 as shown in FIG. 7, which takes on a realistic phallus shape 12, or it may be a more abstract insertion member shape 36 as shown in FIG. 8.

Figure 10:
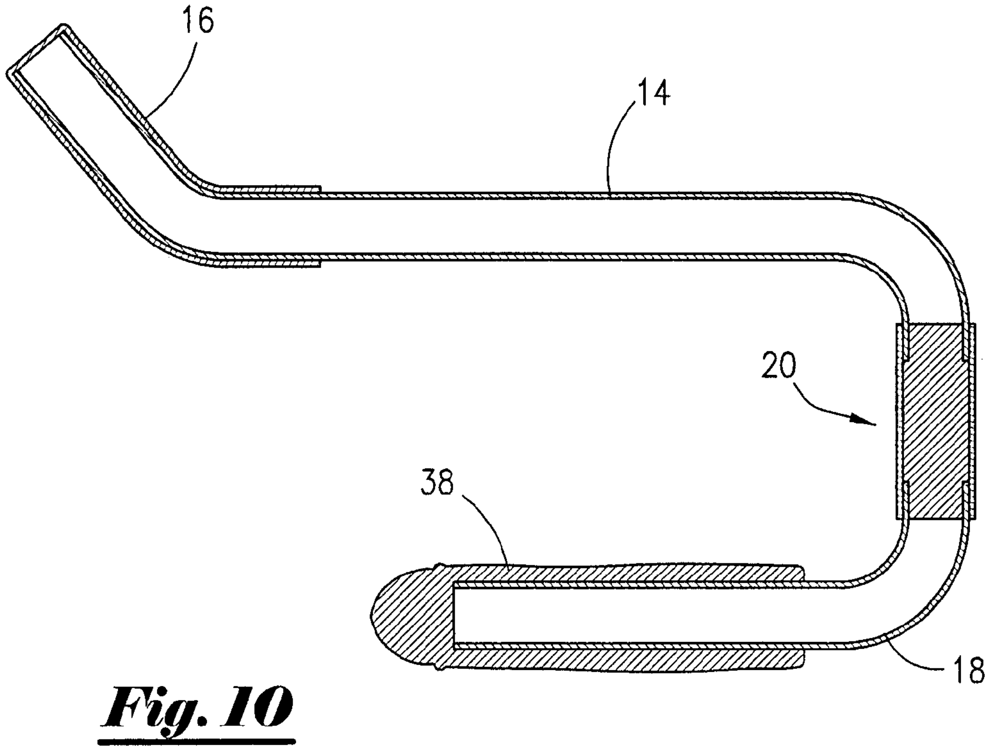
FIG. 10 is a side elevation, cross section view of the embodiment shown in FIG. 9.

Alternatively, the lower tubular member 18 as shown in FIG. 9 may be extended to an approximate equivalent length as that of the appliance 12 and covered by a soft polymeric sleeve 38 having a phallus shape or any desired texture or shape desired. Such sleeves or quick disconnect appliances FIGS. 7,8, may be provided with the handle assembly 10 or purchased separately. The sleeve member 38 may be easily molded for telescopically encompassing the lower tubular member 18 as shown in FIG. 10.

It should also be fully understood that flexure of the tubular member 14 can also be achieve without utilizing the flexible joint 20, heretofore described. By constructing the apparatus 40 using a semi-flexible polymeric bar 42 forming a "J" shape having a pair of vertical portions one of which includes the obtuse angle handle portion and a horizontal portion connecting the vertical portions as seen in FIG. 11, flexure in all planes may be achieved as indicated in FIG. 12. However, the cost in materials may offset any cost savings in construction by eliminating the flexible members 20. Further, use of the flexible joint with rigid or semi-ridged tubing 14 may produce more control in some cases than the fully flexible member 42.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in any limiting sense.

What is claimed is:

1. A sexual aid comprising:

a) an elongated cylindrical member having a first and second end bent to generally define a "J" shape having a short leg portion a straight intermediate portion having a flexible coupling member and a long leg portion having an end portion bent at an obtuse angle; and b) a means for quick coupling a phallus shaped member to an end of said short leg portion.

2. The sexual aid according to claim 1 wherein said elongated cylindrical member is tubular.

3. The sexual aid according to claim 1 wherein said end portion, bent at an obtuse angle further comprises a foam sleeve covering.

4. The sexual aid according to claim 1 wherein said flexible coupling is a polymeric rod.

5. The sexual aid according to claim 1 further comprising a phallus shaped member selected from a variety of sizes and shapes having means for quick coupling to said short leg portion.

6. The sexual aid according to claim 5 wherein said phallus shaped member is a molded sleeve encompassing a tubular portion of said means for quick coupling.

7. The sexual aid according to claim 1 wherein said flexible coupling is a spring.

8. The sexual aid according to claim 1 wherein said means for quick coupling a phallus shaped member is a ball lock quick coupling comprising a first connector members having a plurality of balls located in individual perimeter holes and captured therein by a spring biased sliding sleeve attached to said short leg portion for receiving therein a second connector comprising said phallus shaped member further comprising an elongated cylindrical member having a grooved hub portion at one end for receiving said balls of said first connector member.

9. A sexual aid apparatus comprising:

a) an elongated cylindrical member having a first and second end bent to generally define a "J" shape having a short leg portion a straight intermediate portion having a flexible coupling member and a long leg portion having an end portion bent at an obtuse angle; and b) a phallus shaped sleeve encompassing an end of said short leg portion.

10. The sexual aid according to claim 9 wherein said end portion bent at an obtuse angle further comprise a foam sleeve covering.

11. The sexual aid according to claim 9 wherein said flexible coupling is a polymeric rod.

12. The sexual aid according to claim 9 wherein said elongated cylindrical member is a semi-flexible polymeric.

13. A method for manipulating a dildo comprising the steps of:

a) attaching a dildo to a handle member comprising an elongated rigid handle member having a first and a second end bent to define a "J" shape comprising a short leg portion having snap-on quick coupling means for connecting a dildo, a straight intermediate portion and a long leg portion having an obtuse angle portion;

b) inserting said dildo into a body cavity with said handle member parallel and longitudinal to said body; and c) manipulating said dildo with said handle member.

* * * * *